United States Patent [19]

Gubelmann

[11] Patent Number: 5,274,145

[45] Date of Patent: Dec. 28, 1993

[54] α-HYDROXY-ACIDS, PREPARATION PROCESS AND THE USE THEREOF

[75] Inventor: Michel Gubelmann, Lyons, France

[73] Assignee: Rhone-Poulenc Rorer S.A., Antony, France

[21] Appl. No.: 654,973

[22] Filed: Feb. 14, 1991

[30] Foreign Application Priority Data

Feb. 15, 1990 [FR] France .................. 90 01814

[51] Int. Cl.⁵ .............................. C07C 54/00
[52] U.S. Cl. .................... 554/213; 554/219; 554/223; 554/224
[58] Field of Search ........... 260/405.5; 560/51, 231, 560/126, 179; 562/525; 554/213, 219, 223, 224, 129

[56] References Cited

U.S. PATENT DOCUMENTS 4,585,594 4/1986 Himmele et al. ............... 554/129

OTHER PUBLICATIONS

Gasselin et al., Synthesis, vol. 10, pp. 876–881. 1984.
Chemical Abstracts, vol. 51, No. 17, 12851i, 1957.

Primary Examiner—Jose' G. Dees
Assistant Examiner—Deborah D. Carr
Attorney, Agent, or Firm—Finnegan, Henderson, Farabow, Garrett & Dunner

[57] ABSTRACT

The present invention relates to novel α-hydroxyacids of the general formula (I), to the process of preparing them and to the use thereof as intermediates allowing access to homologous lower aldehydes (such as prenal or citral) by oxidative decarboxylation.

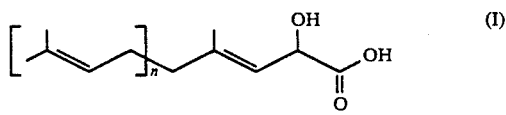

2 Claims, No Drawings

α-HYDROXY-ACIDS, PREPARATION PROCESS AND THE USE THEREOF

BACKGROUND OF THE INVENTION

Field of the Invention

The present invention relates to novel α-hydroxylated β-unsaturated carboxylic acids. In more detail, it relates to novel α-hydroxy-acids of the general formula:

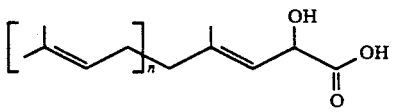

The present invention also relates to the process of preparation and to the use of α-hydroxy-acids of formula (I). In particular, these novel products represent intermediates which provide access, by oxidative decarboxylation, to homologous lower aldehydes (prenal, citral, etc.). Such aldehydes in turn allow access to vitamin A or can also be used for their aroma properties.

It is known from French Patent 1,554,805 to prepare α-ethylenic carbonyl compounds by isomerization of α-acetylenic alcohols. This isomerization takes place by heating the alcohol, optionally in a solvent, in the presence of small quantities of a catalyst based on a metal belonging to groups 3b to 7b of the periodic table of the elements Advantageously, this isomerization takes place in the liquid phase, and the catalyst is an inorganic or organic derivative of a metal selected from the group comprising vanadium, niobium, molybdenum, tungsten and rhenium.

It is also known from U.S. Pat. No. 3,057,888 to prepare unsaturated aldehydes from esters of 1,1-disubstituted propargyl alcohol by heating in an acidic medium in the presence of a catalyst containing a metal belonging to group 1b of the periodic table of the elements.

Moreover, it is known from U.S. Pat. Nos. 2,524,865 and 2,524,866 to prepare ethylenic aldehydes by treating alkynols in the vapour phase under the action of various acidic catalysts. However, this process gives only a ternary mixture of an ethylenic aldehyde, ketone and hydrocarbon.

The present invention describes a novel access route to these aldehydes, and in particular to prenal and citral, from esters of β,γ-unsaturated carboxylic acids. In addition, this route gives very good yields and has made it possible to display and to isolate novel α-hydroxylated β-unsaturated carboxylic acid compounds as intermediates.

SUMMARY OF THE INVENTION

One object of the present invention thus relates to novel compounds of the general formula (I):

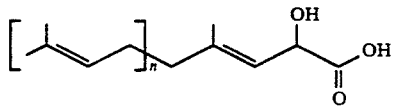

in which n can be 0, 1, 2 or 3.

In particular, the invention relates to compounds of the general formula (I) in which n=0, that is to say 2-hydroxy-4-methyl-pent-3-enoic acid, and n=1, that is to say 2-hydroxy-4,8-dimethyl-nona-3,7-dienoic acid.

Another object of the present invention concerns a preparation process for these compounds of general formula (I) from esters of β,γ-unsaturated carboxylic acids of the general formula (II), set forth below.

The first and second objects of the invention are provided by a process for the preparation of a compound of the general formula (I) comprising:

a first stage wherein an ester of the general formula (II):

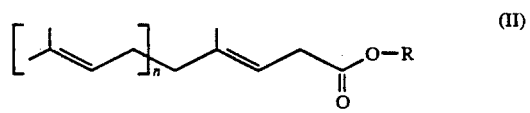

in which R is an alkyl group preferably having 1 to 4 carbon atoms and n is preferably equal to 0, 1, 2 or 3, is saponified to form the corresponding acid, a second stage wherein the dianion of the acid thus obtained is prepared by the action of a base preferably selected from alkali metal hydrides, alkaline earth metal hydrides, alkali metal amides and organometallic alkyls, in an organic solvent, and a third stage wherein the dianion is oxygenated to form the acid of the formula (I).

A third object of the present invention relates to the use of these novel compounds for the preparation of homologous lower aldehydes by oxidative decarboxylation by means of an oxidizing agent.

The third object of this invention is accomplished by a method for the preparation of homologous lower aldehydes of the compound of the general formula (I) wherein the compound undergoes oxidative decarboxylation by means of an oxidizing agent.

DETAILED DESCRIPTION

In the process of this invention, the first stage involves the following reaction: saponification of the ester (II) to produce the acid of the general formula (III)

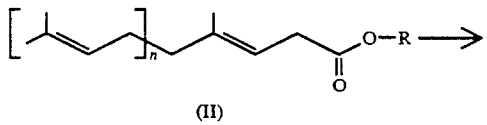

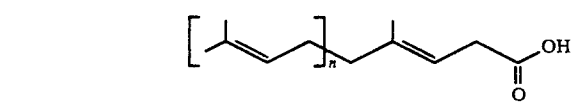

In a particular embodiment of the invention, R which can be an alkyl group having preferably 1 to 4 carbon atoms is a methyl group, and n, which can be 0, 1, 2 or 3, is equal to 0 (methyl 4-methyl-pent-3-enoate) or equal to 1 (methyl 4,8-dimethyl-nona-3,7-dienoate).

The saponification reaction can be carried out by means of a strong base of the M—OH type, in which M is preferably an alkali metal or a quaternary ammonium group, in an organic solvent. In particular, this can be effected in water-miscible solvents, including alcohols such as methanol, ethanol, isopropanol etc. In a preferred embodiment of the invention, methanolic sodium hydroxide can be used.

The reaction temperature is preferably between ambient temperature and the reflux temperature of the mixture.

The esters of the general formula (II) can be prepared from isoprene, or a higher homologue, according to the process described in French Patent FR 81 01,205, which is incorporated specifically by reference herein. The reaction can be conducted as follows:

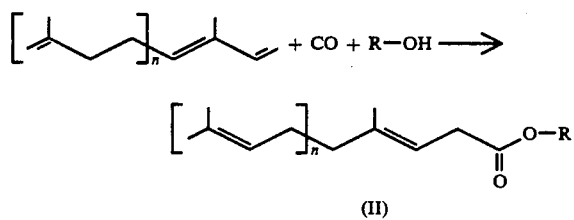

(II)

This carbonylation reaction can be effected by means of carbon monoxide in the presence of an alcohol, R—OH, corresponding to the desired ester and preferably in the presence of at least one of the following: a hydrohalic acid (in particular hydrochloric acid or hydrobromic acid) and a palladium catalyst (palladium metal, palladium oxide, a palladium salt or complex whose anion coordinated with the palladium cation is a "hard" or "intermediate" base) and more preferably in the presence of a hydrohalic acid, a palladium catalyst and a quaternary onium salt of a group Vb element selected from nitrogen, phosphorus and arsenic, at a temperature ranging from about 50 to about 150° C. and under a carbon monoxide pressure ranging from about 50 to about 300 bars. Under these conditions, the ester can be obtained in very good yields.

With respect to the second stage of the present process, the preparation of the dianion of the acid (III), the following procedure can be employed:

The dianion can be obtained by the action of a base such as the alkali or alkaline earth metal hydrides or amides, or the organometallic alkyls, deposited or grafted on a support if desired, in an organic solvent. According to the present invention, the alkali metal amide can be selected from lithium diisopropylamide (LDA) which can be prepared "in situ" by the action of butyllithium on diisopropylamine, sodium tert.-butylate or also sodium amide.

The hydrides which can be used in this reaction are preferably hydrides of sodium, potassium or calcium. With respect to the organometallic alkyls, organolithium compounds, organomagnesium compounds and the sodium or potassium alkyls can be used. Specifically, butyllithium is most preferred.

In a preferred embodiment of the invention, LDA is used as the base.

In the case of heterogeneous bases, oxide-type supports, for example, can be used, preferably aluminas. In this connection, potassium tert.butylate and potassium fluoride on alumina may be mentioned as heterogeneous bases.

With respect to the organic solvent, all ether-type solvents can be suitable for this reaction. Preferably, tetrahydrofuran. diisopropyl ether, methyl tert.-butyl ether or paradioxane is used. In a most preferred embodiment, tetrahydrofuran is used.

Finally, the reaction of forming the dianion is advantageously carried out at low temperature and preferably at temperatures ranging from about −20° C. to about +20° C., more preferably from about −10° C. to about +10° C. In certain cases, the temperature can temporarily be raised at the end of the reaction to shift the equilibrium of the reaction as far as possible towards formation of the dianion. This thermal finishing treatment preferably takes place at temperatures ranging from 20° C. to 50° C., and more preferably from 30° C. to 40° C.

The third stage of the present process, which concerns the oxygenation of the dianion, is preferably carried out as follows.

The oxygenation of the dianion to produce the α-hydroxy-acid of the general formula (I) is effected by means of oxygen or air, optionally enriched with oxygen, and more preferably by air. It can be carried out by allowing the oxygen or air to come into contact with a stirred solution of the dianion, or by sweeping across the surface of the said solution. In another embodiment, the oxygenation can be achieved by means of pressurized air. Advantageously, this reaction is preferably carried out after the temperature is close to ambient temperature.

When the process which is the subject of the invention is carried out, secondary products can form in which the oxygenation has not taken place in the α-position of the acid. However, these products can arise in very subordinate amounts and, because of their low degree of crystallization, they can be eliminated by filtration after the crystallization of the main products.

The third object of the present invention relates to the use of these novel compounds for the preparation of homologous lower aldehydes by oxidative decarboxylation by means of an oxidizing agent, as follows:

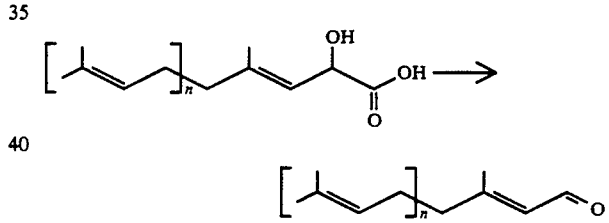

This reaction can be carried out by means of an oxidizing agent such as an acetate of one or more metals selected from cobalt, manganese, lead, silver or the copper-lead couple, and preferably selected from cobalt and lead. In particular, lead tetraacetate gives very good results.

It is equally possible to effect the oxidative decarboxylation indirectly by the free-radical techniques described by Maumy et al. (Tetrahedron Letters, 1983, 3819), specifically incorporated by reference herein. In particular, metals, especially those such as Cu$_2$O, can be used in a solvent which stabilizes copper (I), such as acetonitrile, at atmospheric pressure.

Other subjects and advantages of the present invention will be appreciated by reading the examples which follow and which are to be considered as illustrate and not limit the invention.

EXAMPLE 1 Synthesis of 4-methyl-pent-3-enoic acid by saponification of methyl 4-methyl-pent-3-enoate 12.8 g (100 mmol) of the ester methyl 4-methyl-pent-3-enoate are used, which are diluted with 50 ml of methanol. 15 ml of 30% sodium hydroxide solution (112 mmol) are added dropwise. The solution obtained is heated under reflux for 3 hours with stirring. The solvent is then evaporated to dryness and the remaining carboxylate is treated with 15 ml of concentrated HCl. The acid is then extracted with ether and the extract is dried over $Na_2SO_4$. The ether is then evaporated and the last traces of water are eliminated under a vane-pump vacuum. Under these conditions, the conversion rate of the ester is 100% and the yield is 92%.

EXAMPLE 2 Preparation of 2-hydroxy-4-methyl-pent-3-enoic acid 4 g of diisopropylamine in solution in 60 ml of anhydrous tetrahydrofuran are introduced under an argon atmosphere into a three-necked 250 ml reactor fitted with a central stirrer, a condenser, a 50 ml dropping funnel, a gas inlet and a heating system. The reactor is cooled by means of an ice bath, and 37 ml of a 1.1M solution of butyllithium in hexane are then added dropwise while maintaining the temperature below 5° C. After stirring for 30 minutes at a temperature of 2° C., a solution of 2.28 g of 4-methyl-pent-3-enoic acid in 30 ml of anhydrous tetrahydrofuran is added. After stirring for 30 minutes, the reaction mixture is heated for 1 hour at 40° C.

After cooling to a temperature close to 20° C., air is introduced for 3 hours by means of a balloon, always with vigorous stirring. The reaction is followed by determination of the acids by proton nuclear magnetic resonance at 360 MHz.

After the reaction has ended, two 250 ml portion of water are added.

The aqueous phase which has been separated off by decanting is concentrated and then acidified with concentrated hydrochloric acid and finally extracted with ether.

The other phases, after drying and concentrating, give an oil which slowly crystallizes on cooling.

The crude product obtained contains 90% of 2-hydroxy-4-methyl-pent-3-enoic acid and 10% of 4-hydroxy-4-methyl-pent-3-enoic acid.

The 2-hydroxy-4-methyl-pent-3-enoic acid is separated off by filtration over fritted glass.

The 2-hydroxy-4-methyl-pent-3-enoic acid has the following physico-chemical characteristics:

melting point: 95°-98° C.

elemental analysis: C% calculated: 55.37 found: 54.76 H% calculated: 7.75 found: 7.28 infrared spectrum (KBr pellet), characteristic bands at: 3400 $cm^{-1}$ (alcoholic OH), 3100-2300 $cm^{-1}$ (acidic OH), 2980 $cm^{-1}$ ($CH_3$), 1705 $cm^{-1}$ (C=O, acid) and 1070 $cm^{-1}$ (C—O, alcohol)

proton nuclear magnetic resonance spectrum (360 MHz, $CDCl_3$, chemical shifts in ppm relative to hexamethyldisilane taken as reference): 5.13 (d, 1H,=CH—); 4.85 (d, 1H,=CH—CH(OH)—); 1.72 (2s, 6H, $2\times CH_3$)

mass spectrum (m/e): $M^+=130$.

The conversion rate of the 4-methyl-pent-3-enoic acid is 58%.

EXAMPLE 3 Preparation of 2-hydroxy-4-methyl-pent-3-enoic acid

The procedure of Example 2 is followed, but by sweeping the surface with air.

The conversion rate of 4-methyl-pent-3-enoic acid is 100%.

2-Hydroxy-4-methyl-pent-3-enoic acid is isolated in a yield of 87%.

4-Hydroxy-4-methyl-pent-3-enoic acid is obtained in a yield of 5%.

EXAMPLE 4 - Preparation of prenal from the α-hydroxy-acid 0.143 g of 2-hydroxy-4-methyl-pent-3-enoic acid, 5 ml of an aqueous solution containing 90% of acetic acid and 0.54 g of lead tetraacetate are introduced into a 50 ml flask fitted with a magnetic stirrer. The mixture is stirred for 1 hour at 25° C. 5 ml of 0.35M sulphuric acid are added, and the precipitated lead sulphate is separated off by filtration. The prenal is quantitatively precipitated in the filtrate in the form of the 2,4-dinitrophenylhydrazone.

The yield is 70.3%.

EXAMPLE 5 Preparation of prenal from the α-hydroxy-acid 0.143 g of 2-hydroxy-4-methyl-pent-3-enoic acid, 5 ml of 1,2-dichlorobenzene and, in small portions, 0.54 g of lead tetraacetate are introduced into a 50 ml flask fitted with a magnetic stirrer. The mixture is stirred for 1 hour at 25° C. After decanting, analysis of the reaction mixture by gas chromatography shows that the conversion rate of the 2-hydroxy-4-methyl-pent-3-enoic acid is 100% and that the yield of prenal is 86%.

I claim:

1. A compound of the general formula (I):

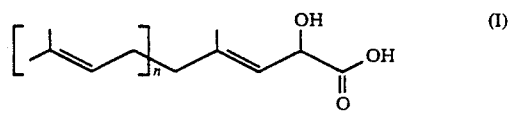

in which n is equal to 1, 2 or 3.

2. A compound according to claim 1 wherein n=1.

* * * * *